United States Patent [19]

Widmer

[11] Plant 4,327

[45] Oct. 31, 1978

[54] CHRYSANTHEMUM NAMED MINNGOPHER

[75] Inventor: Richard E. Widmer, St. Paul, Minn.

[73] Assignee: Regents of The University of Minnesota, Minneapolis, Minn.

[21] Appl. No.: 797,496

[22] Filed: May 16, 1977

[51] Int. Cl.[2] ..... A01H 5/00

[52] U.S. Cl. ..... Plt./75

[58] Field of Search ..... Plt./75, 81–82

*Primary Examiner*—Robert E. Bagwill

*Attorney, Agent, or Firm*—Chas. W. Rummler

[57] ABSTRACT

A new and distinct cultivar of chrysanthemum of the outdoor garden and greenhouse pot plant type characterized by its dark red, medium sized blooms of decorative flower form which appear in an open spray formation, its ability to be flowered the year around with uniform 6-week response under photoperiod control, and by its excellent performance as a spring, summer and fall potted plant and as a natural season garden flower.

3 Drawing Figures

BACKGROUND OF THE NEW PLANT

This new variety of chrysanthemum plant originated as a seedling resulting from a cross of Ruby Mound (unpatented) and an unnamed and unpatented variety, identified in my records as MN Se. 67-111-184, made by me in 1970 at St. Paul, Minn., during the course of breeding efforts carried on by me at St. Paul, Minn., since 1968 with the object of developing new and better chrysanthemum varieties. The distinctive dark red color of the medium sized blooms of this plant and its short compact growth caused me to select this plant for propagation and test, which was done by me at St. Paul, Minn., by means of cuttings from the original plant. The plants so reproduced appeared to have all of the novel and distinctive features of the original plant and subsequent propagation of this variety by vegetative cuttings at West Chicago, Ill., and at Cortez, Fla., has demonstrated that the distinctive characteristics of this new variety hold true from generation to generation and are firmly fixed.

DESCRIPTION OF THE DRAWINGS

This new chrysanthemum plant is illustrated by the accompanying drawings, the first of which is a photographic print in full color showing a potted plant in full bloom, the colors shown being as nearly true as it is reasonably possible to obtain by conventional photographic procedures and the photograph being of a cultivar of this variety grown at West Chicago, Ill., and flowered in March 1977. The second sheet of the drawings is a mechanical print of a photocopy of typical leaves of this new plant at several stages of maturity.

DESCRIPTION OF THE NEW PLANT

The following is a detailed description of my new chrysanthemum cultivar with color designations according to the R.H.S. Colour Chart published by The Royal Horticultural Society at London, England, the observations having been made of plants reproduced and grown at West Chicago, Ill.

THE PLANT

Origin: Seedling.

Parentage:

*Seed parent.*—Ruby Mound (unpatented).

*Pollen parent.*—An unnamed and unpatented variety identified as MN Sel. 67-111-184.

Classification:

*Botanic.*—*Chrysanthemum Morifolium.*

*Commercial.*—Greenhouse pot plant and outdoor garden plant.

Form: Perennial herbaceous bush.

Height:

*As a pot plant.*—About 4½ to 7 inches.

*As an outdoor garden plant.*—About 11 to 15 inches.

Growth: Terminal, with a low spreading habit, sturdy with very good strength.

Branching: Under natural conditions.

Foliage: Quantity — abundant with seven to nine leaves per 4 inches of stem.

Leaf size: About 1¼ to 2½ inches long.

*Shape.*—Lanceolate, lobed and deeply serrated.

*Color.*—Upper side — Yellow-Green 147A. Under side — Yellow-Green 147B.

*Surface texture.*—Canescent.

*Venation.*—Pinnately veined.

Petioles: Length — About 3/16 to ⅜ inch.

THE BUD

Form: Elliptical.

Size:

*Diameter.*—About ¼ to ½ inch.

*Depth.*—About 3/16 to ⅜ inch.

Opening: The bud opens slowly.

Color:

*When phyllaries first divide.*—Yellow-Green 144A.

*When florets begin to unfurl.*—Greyed-Purple 185A.

Phyllaries: The outside of the receptacle bears many phyllaries as involucral bracts.

*Form.*—Spear-shaped and upstanding.

*Color.*—Inside surface — Yellow-Green 146B. Outside surface — Yellow-Green 147B.

*Surface texture.*—Pubescent.

Peduncle: Length — About ½ to ¾ inch.

*Surface Texture.*—Pubescent.

*Strength.*—Erect and strong.

*Color.*—Yellow-Green 148C.

THE FLOWER

Blooming capability: This plant can be flowered the year around with photoperiod control.

*Response.*—6 weeks.

*Recommended flowering.*—March 1 to November 1.

*Natural flowering season.*—About September 26 to October 9.

Blooms:

*Flower type.*—Composite and decorative.

*Size.*—Medium. Diameter: About 1½ to 2½ inches. Depth: About ⅝ to 1 inch.

*Shape.*—Flat when bloom first opens, becoming more hemispherical as the bloom matures.

*Borne.*—Singly, as a head of many florets on a receptacle, in a relatively open spray formation.

*Florets.*—Numerous in quantity. Form: Linear with obtuse apex. Arrangement: Decorative. Texture. Medium Firm. Appearance: Very slight shine. Discoloration: Very little fade.

Color:

| | March | April | October | November |
|---|---|---|---|---|
| Outer petals: | | | | |
| Upper side - | 46A | 45A and B | 46A | 46A |
| Reverse - | 181A | 180A | 42B | 180A |
| Inside petals: | | | | |
| Upper side - | 187A | 46A | 46A | 187B |
| Reverse - | 187A | 179A and B | 46A | 187C |

*General color tonality of bloom.*—When viewed from a distance of 6 feet; March — 46B; April — 45B and C.

*Effect of Weather.*—Flower is not affected by hot or wet weather

*Persistence.*—Florets hang on and dry.

*Fragrance.*—Typical chrysanthemum.

*Lasting quality.*—On plant — 3 weeks. As cut flower — Not recommended for cut flowers.

REPRODUCTIVE ORGANS

Stamens: Number five, syngenesiously arranged.

*Filaments.*—Length—About $\frac{1}{16}$ to $\frac{1}{8}$ inch. Color — Light Yellow.

*Pollen.*—Color — Yellow.

Pistils: Number — One to each disc and ray floret.

*Styles.*—About $\frac{1}{8}$ to 3/16 inch long.

*Stigmas.*—Color — Yellow.

Ovaries: Inferior bicarpellate.

My new chrysanthemum cultivar is particularly distinguished by the dark red color of the medium sized decorative form of its blooms which are presented in an open spray formation, and by its uniform 6-week photoperiodic flowering response. This plant has excellent performance as a 4 to 5 inch potted plant for spring, summer and fall culture and as a natural season garden chrysanthemum. It has a short, compact plant habit which requires no growth retardant, and grows with strong stems and abundant small to medium sized foliage.

I claim:

1. A new and distinct chrysanthemum cultivar substantially as herein shown and described, characterized by the dark red color of its medium sized blooms of decorative form displayed in an open spray formation on a short compact plant particularly suited for greenhouse pot plant culture and for outdoor garden growth.

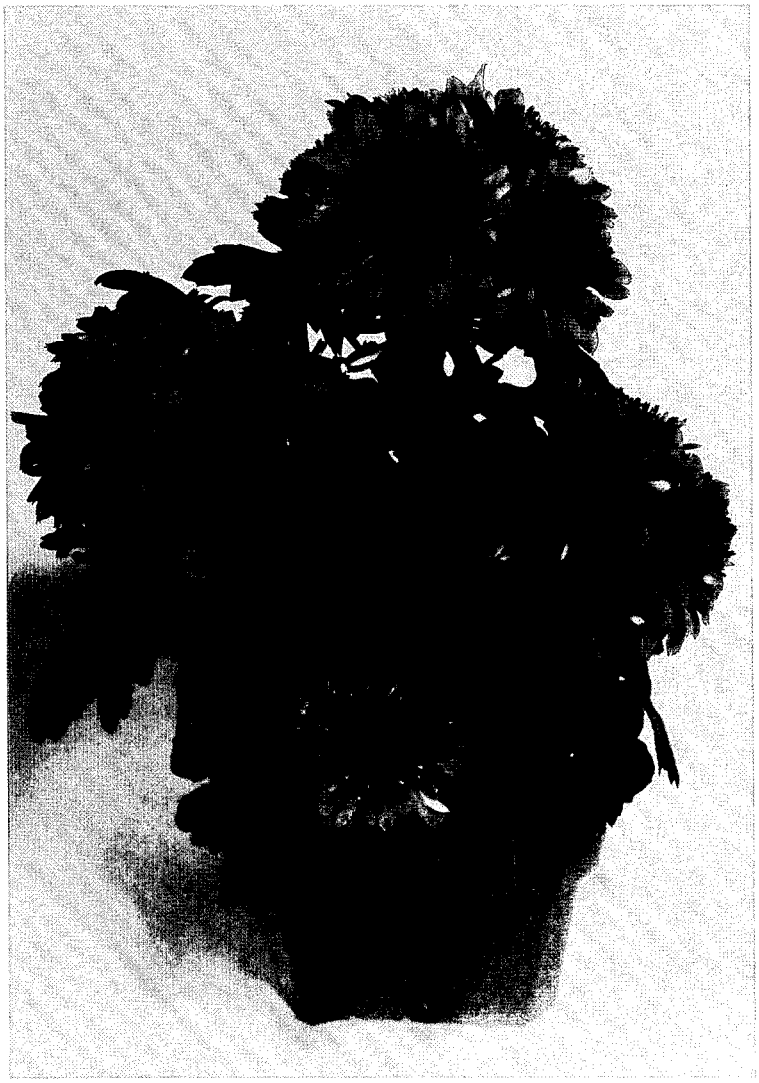

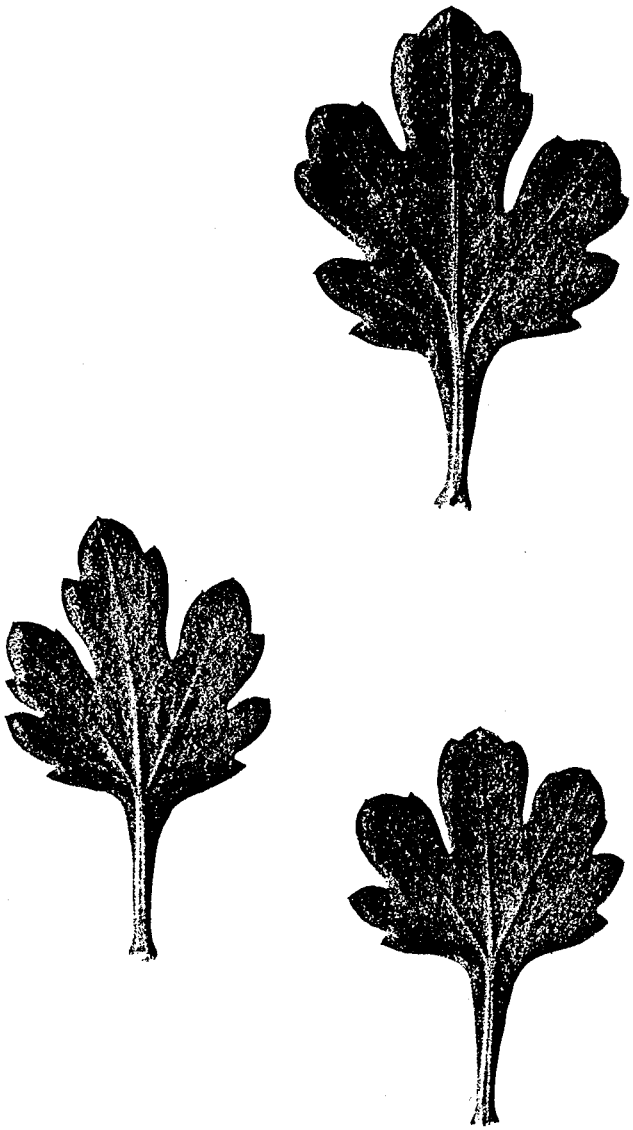

* * * * *